(12) United States Patent
Roach et al.

(10) Patent No.: US 9,121,817 B1
(45) Date of Patent: Sep. 1, 2015

(54) ULTRASONIC TESTING DEVICE HAVING AN ADJUSTABLE WATER COLUMN

(75) Inventors: Dennis P. Roach, Albuquerque, NM (US); Stephen O. Neidigk, Albuquerque, NM (US); Kirk A. Rackow, Albuquerque, NM (US); Randy L. Duvall, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 381 days.

(21) Appl. No.: 13/544,177

(22) Filed: Jul. 9, 2012

Related U.S. Application Data

(60) Provisional application No. 61/660,264, filed on Jun. 15, 2012.

(51) Int. Cl.
*G01N 29/28* (2006.01)

(52) U.S. Cl.
CPC ..................... *G01N 29/28* (2013.01)

(58) Field of Classification Search
CPC ..... G01N 29/28; G01N 29/24; G01N 29/227; G01N 29/228; G01N 29/2468
USPC .................................................. 73/644, 633
See application file for complete search history.

(56) References Cited

U.S. PATENT DOCUMENTS

| | | | |
|---|---|---|---|
| 3,555,891 A * | 1/1971 | Lewis | 73/644 |
| 3,946,599 A * | 3/1976 | Patt | 73/644 |
| 4,033,178 A * | 7/1977 | Holt et al. | 73/644 |
| 4,183,249 A | 1/1980 | Anderson | |
| 4,472,975 A | 9/1984 | Beck et al. | |
| 5,060,201 A | 10/1991 | Ishikawa et al. | |
| 5,343,109 A | 8/1994 | Mockl | |
| 5,469,744 A | 11/1995 | Patton et al. | |
| 5,494,038 A | 2/1996 | Wang et al. | |
| 5,729,508 A | 3/1998 | Baker et al. | |
| 5,814,731 A | 9/1998 | Alexander et al. | |
| 6,298,727 B1 | 10/2001 | Fleming et al. | |
| 6,481,190 B2 | 11/2002 | Van Zanten et al. | |
| 6,733,457 B2 | 5/2004 | Flesch et al. | |
| 6,948,369 B2 | 9/2005 | Fleming et al. | |
| 7,284,434 B1 | 10/2007 | Fleming | |
| 7,311,679 B2 | 12/2007 | Desilets et al. | |
| 7,694,569 B2 | 4/2010 | McGrath et al. | |
| 7,926,344 B1 | 4/2011 | Hyde et al. | |
| 2003/0192382 A1 * | 10/2003 | Mueller | 73/620 |

OTHER PUBLICATIONS

Hsu, D.K., et al., "Detection and imaging of corrosion around wing skin fasteners using the dripless bubbler ultrasonic scanner," SPIE vol. 3397, (1998), pp. 32-38.

Hsu, D.K., et al., Nondestructive Evaluation of Repairs on Aircraft Composite Structures, SPIE vol. 4336, (2001), pp. 100-107.

* cited by examiner

*Primary Examiner* — Laura Martin
*Assistant Examiner* — Rose M Miller
(74) *Attorney, Agent, or Firm* — Daniel J. Jenkins

(57) ABSTRACT

An ultrasonic testing device having a variable fluid column height is disclosed. An operator is able to adjust the fluid column height in real time during an inspection to to produce optimum ultrasonic focus and separate extraneous, unwanted UT signals from those stemming from the area of interest.

10 Claims, 9 Drawing Sheets

ULTRASONIC TESTING DEVICE HAVING AN ADJUSTABLE WATER COLUMN

CROSS-REFERENCE TO RELATED APPLICATIONS

This application is a nonprovisional of U.S. Provisional Patent Application 61/660,264, filed Jun. 15, 2012, entitled "Ultrasonic Testing Device Having an Adjustable Water Column, the disclosure of which is incorporated by reference in its entirety.

This application is related to U.S. patent application Ser. No. 13/237,520, filed Sep. 20, 2011, entitled "Ultrasonic Probe Deployment Device for Increased Wave Transmission and Rapid Area Scan Inspections", which is a Continuation of application Ser. No. 12/401,321, filed Mar. 10, 2009, now allowed, entitled "ULTRASONIC PROBE DEPLOYMENT DEVICE FOR INCREASED WAVE TRANSMISSION AND RAPID AREA SCAN INSPECTIONS", and U.S. Pat. No. 6,234,025, filed Mar. 29, 1999, entitled ULTRASONIC INSPECTION APPARATUS AND METHOD USING A FOCUSED WAVE DEVICE", whose disclosures are incorporated by reference in their entirety.

STATEMENT REGARDING FEDERALLY SPONSORED RESEARCH OR DEVELOPMENT

The United States Government has certain rights in this invention pursuant to Department of Energy Contract No. DE-AC04-94AL85000 with Sandia Corporation.

FIELD OF THE INVENTION

This invention relates generally to ultrasonic inspection, and more particularly to an ultrasonic testing (UT) device including a housing that can adjust the signal-transmitting water column height in real-time.

BACKGROUND OF THE INVENTION

Composites have many advantages for use as aircraft structural materials including their high specific strength and stiffness, resistance to damage by fatigue loading and resistance to corrosion. Multiple industries, most notably the aircraft industry, continue to increase their use of composite materials, most noteworthy in the arena of principle structural elements. This expanded use, coupled with difficulties associated with damage tolerance analysis of composites, has placed greater emphasis on the application of accurate nondestructive inspection (NDI) methods.

In addition, advances in structural adhesives have permitted engineers to contemplate the use of bonded joints in areas that have long been dominated by mechanical fasteners and welds. The deployment of bonded joints generally requires the use of sensitive nondestructive inspection techniques to ensure the continued integrity of the bond joint. Adhesive bonding is being used in the manufacture of high performance components such as wind turbine blades, civil structures and aircraft.

These components may be formed of highly-attenuative materials of varying thickness. Such high performance applications require highly sensitive flaw detection. However, current quality control relies primarily on the robust control of the production process, the adhesive preparation and/or the careful application of materials. However, there is no practical method currently available to assess the overall quality of the composite structure or adhesive joints with sufficient sensitivity.

Additionally, installed adhesive bonded structures, such as wind turbine blades and aircraft components may incur failure or degradation. A typical aircraft can experience over 2,000 fatigue cycles (cabin pressurizations) and many more flight hours in a single year. Wind turbine blades can experience millions of fatigue cycles in a single year of operation. The unavoidable by-product of this use is that flaws develop throughout the structure's skin and substructure elements. The main causes of structural failure in these components are environmental degradation, adhesive disbonds, interply delaminations, and subsurface fiber fracture due to impact. When these types of damage occur, they may lead to catastrophic failures. By their nature, they occur at an interface and are, therefore, always hidden. A combination of fatigue loads and other environmental weathering effects can combine to initiate these types of flaws. A periodic inspection of composites for disbonds and delaminations (from fabrication, installation, fatigue, or impact damage) is essential to assure the successful operation of the structure over time. The interactions at the bond interface are extremely complex, with the result that the strength of the bond is difficult to predict or measure. Even a partial disbond may compromise the integrity of the structural assembly. Therefore, it is necessary to detect all areas of disbonding or delamination before joint failures can occur.

As the commercial airline industry responds to calls for the ensured airworthiness of global airline fleets, inspection reliability is of growing importance. The development and application of new Nondestructive Inspection (NDI) techniques needs to keep pace with the growing understanding of aircraft structural aging phenomena. Ultrasonic inspection or testing is a nondestructive method in which beams of high frequency sound waves are introduced into materials for the detection of surface and subsurface flaws in the material. In ultrasonic pulse-echo inspections, short bursts of ultrasonic energy are interjected into a test piece at regular intervals of time. In most pulse-echo systems, a single transducer acts alternately as the sending and receiving transducer. Sometimes it is advantageous to use separate sending and receiving transducers for pulse-echo inspection.

The sound waves, normally at frequencies between 0.1 and 25 MHz, travel from the transducer through a water column within the inspection device and into the material with some attendant loss of energy (attenuation) and are reflected at interfaces within the test article. The water column between the ultrasonic transducer and the inspection surface produces the signal coupling needed to interrogate the test article.

The reflected beam is displayed and then analyzed to define the presence and location of flaws. The degree of reflection depends largely on the physical state of the materials forming the interface. Fracture, delaminations, shrinkage cavities, pores, disbonds, and other discontinuities that produce reflective interfaces can be detected. Complete reflection, partial reflection, scattering or other detectable effect on the ultrasonic waves can be used as the basis of flaw detection. In addition to wave reflection, other variations in the wave, which can be monitored, include: time of transit through the structure to be inspected, attenuation, and features of the spectral response.

In traditional ultrasonic inspection devices, the height of the water column (the distance that the sound waves travel from the transducer to the test article or device signal travel distance) is fixed. Depending on the total travel distance (the sum of the fixed transducer travel distance and the penetration depth), the reflected signal may include noise and/or masking signals from harmonics or other undesirable reflections within the part. An operator may use a single or several ultrasonic inspection devices having a selected fixed transducer travel distance or distances to try to minimize noise and/or avoid the presence of masking signals created by signal harmonics or other undesirable reflections.

However, these fixed transducer standoff devices are not capable of adjusting the water path distance to shift the undesirable masking signals away from the true signals of interest. Often, parts being inspected do not have a fixed thickness, where the signals of interest vary and can at certain thicknesses be masked by front surface signal multiples. When inspecting parts of varying thickness, it is necessary to adjust the distance between the ultrasonic transducer and the surface of the test article so that the unneeded harmonic signals do not interfere with the signals of interest. In addition, it is necessary to suspend a water column between the ultrasonic transducer and the inspection surface in order to produce the signal coupling needed to interrogate the test article.

Thus, there is a need for ultrasonic inspection device that can vary the device signal travel distance.

SUMMARY OF THE INVENTION

The present invention overcomes these difficulties encountered with prior art ultrasonic inspection devices having fixed device signal travel distance. The present invention overcomes the limitations of the prior art by providing an ultrasonic inspection device including a housing that can vary or adjust the height of the water column that couples the transducer to the test article. This invention allows for maximum signal strength and ultrasonic sensitivity by allowing for real-time adjustments in the offset distance between the ultrasonic transducer and the component being inspected. It allows for accurate detection of flaws in structures and is especially useful in high-attenuation structures and those with thick and varying-thickness laminates. When using the present invention, a noticeable improvement in the pulse echo response can be obtained. Signals of interest can be separated from undesirable signals that are an impediment to the ultrasonic inspection process. This, in turn, produces improved damage detection and additional sensitivity through increased signal-to-noise ratios in the resultant data.

The ultrasonic probe deployment device described above has many advantages as described in the following (not all implementations will have all of the listed features). Water column height within the housing can be adjusted to optimize the distance between the inspection site and the ultrasonic transducer. This adjustment allows users to accurately and repeatably focus the ultrasonic waves at a particular depth/region for maximum sensitivity and resolution in real time. In an embodiment, a position encoder synchronizes movement of the device with the ultrasonic data acquisition, thus allowing the generation of area images (e.g., C-Scan inspection images). These images are generally easier for a field inspector to interpret compared to A or B-Scan ultrasonic signals. This also facilitates the location and sizing of flaws.

In an embodiment, an ultrasonic testing device is disclosed that includes an outer housing and a transducer disposed within an inner housing. The device includes an outer housing and an inner housing adjustably connected to the outer housing. The outer housing includes an interior surface that at least partially defines a fluid cavity having a water column height. The inner housing is adjustably connected to the outer housing to increase and decrease the water column height.

In another embodiment, a method is disclosed that includes a method of ultrasonic testing that includes placing an ultrasonic testing device having an adjustable fluid column height upon a test article, providing fluid to the ultrasonic testing device, generating ultrasonic waves from a transducer within the ultrasonic inspection device, and adjusting the fluid column height to perform an ultrasonic inspection scan of an article.

An object of the present invention is to improve the sensitivity of ultrasonic pulse echo inspections.

Another object of the present invention is to utilize water or other fluid columns to transmit the ultrasonic signal with maximum efficiency (strength) from the transducer to the component being inspected.

An advantage of the present invention is that the resulting inspections are of higher quality and can be completed faster than current alternatives.

Another advantage of the present invention is the improved sensitivity of conventional A-scans and C-scans using ultrasonic pulse echo techniques for the inspection of structures.

Another advantage of the present invention is the ability to detect disbonds and delaminations in composite articles due to improved sensitivity at structure interfaces. Adjustments in the height of the signal-coupling fluid column allow signals of interest to be separated from undesirable signals and more easily recognized.

Another advantage of the present invention is increased signal clarity in varying thickness parts while providing a coupling water column where no additional ultrasonic couplant is needed on the surface of the part. It is a robust housing suitable for field deployment in industrial settings.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instruments and combinations particularly pointed out in the appended claims.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict embodiments of the present invention for purposes of illustration only, and are not necessarily drawn to scale. One skilled in the art will readily recognize from the following discussion that alternative embodiments of the structures and methods illustrated herein may be employed without departing from the principles of the invention described herein.

DETAILED DESCRIPTION

Figure 1:
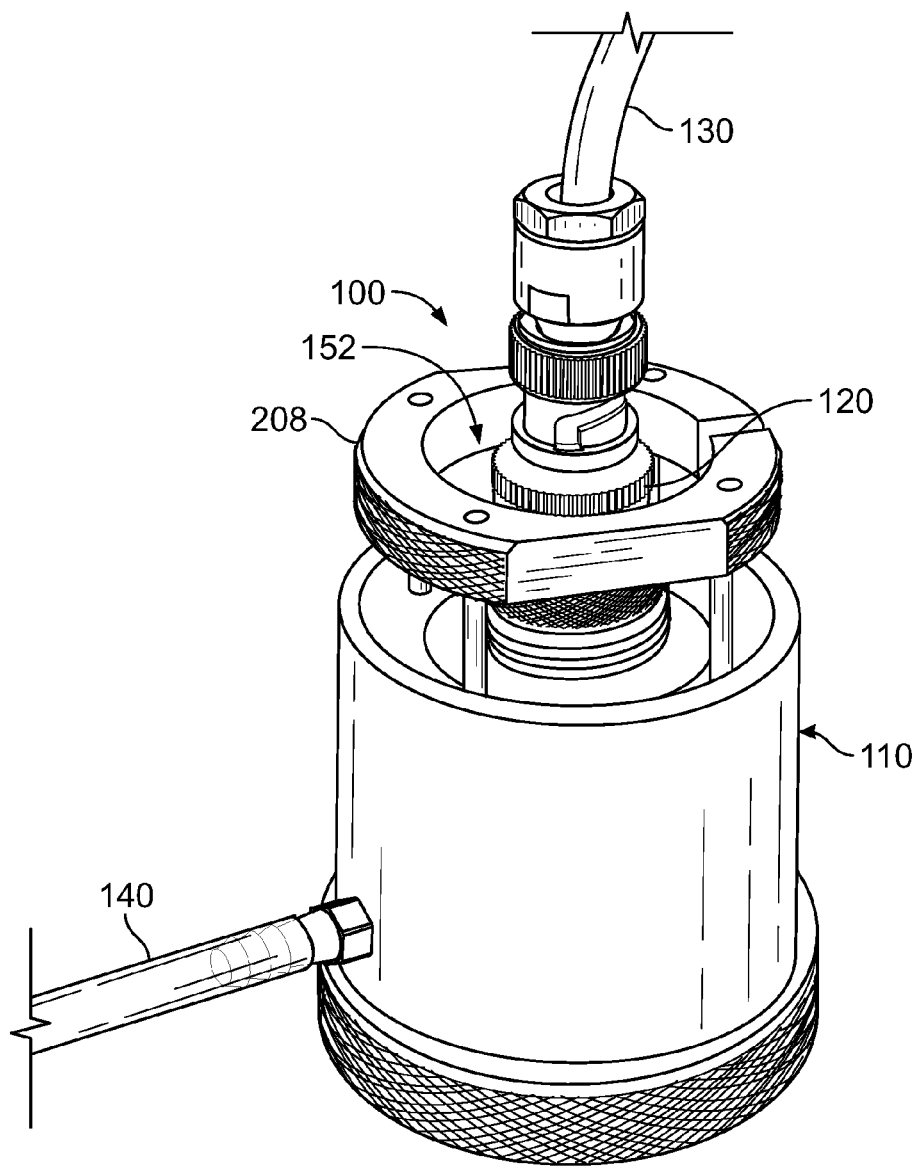
FIG. 1 is an illustration of an embodiment of an ultrasonic testing device according to the invention.
Figure 1A:
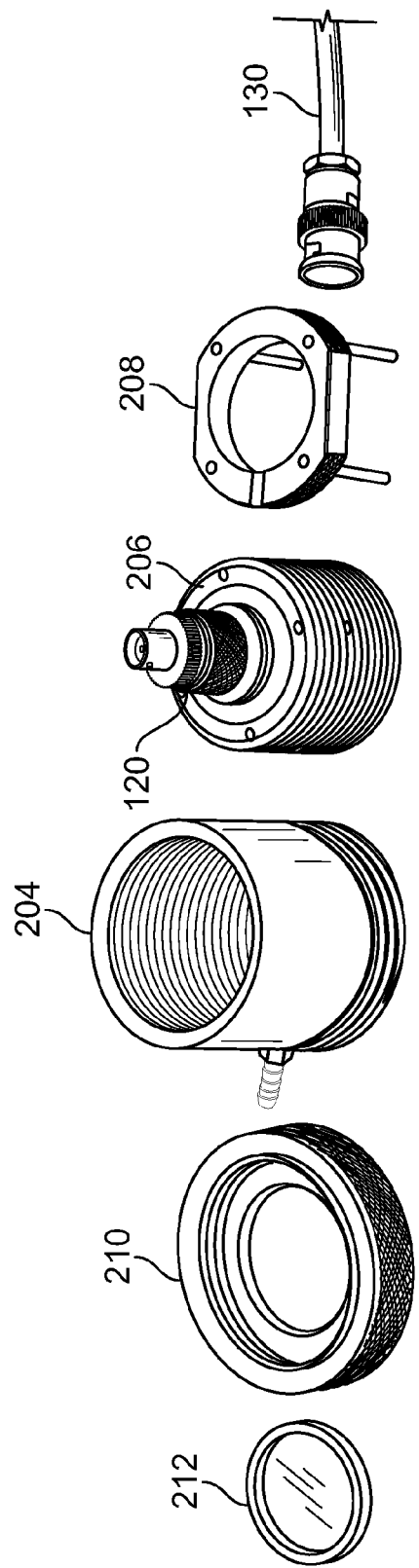
FIG. 1A shows the ultrasonic testing device of FIG. 1 partially dissembled.

FIGS. 1 and 1A illustrate an ultrasonic testing (UT) device 100 according to the present invention. As can be seen in FIG. 1, the UT device 100 includes a housing system 110, a transducer 120 attached to the housing system 110, a signal transmission link 130 coupled to the transducer 120, and a fluid line 140 coupled to the housing system 110. The UT device further includes an optional height control device 208. The UT device 100 is disposed or positioned upon an inspection surface 150 of a test article 160 (see FIG. 5).

Figure 2:
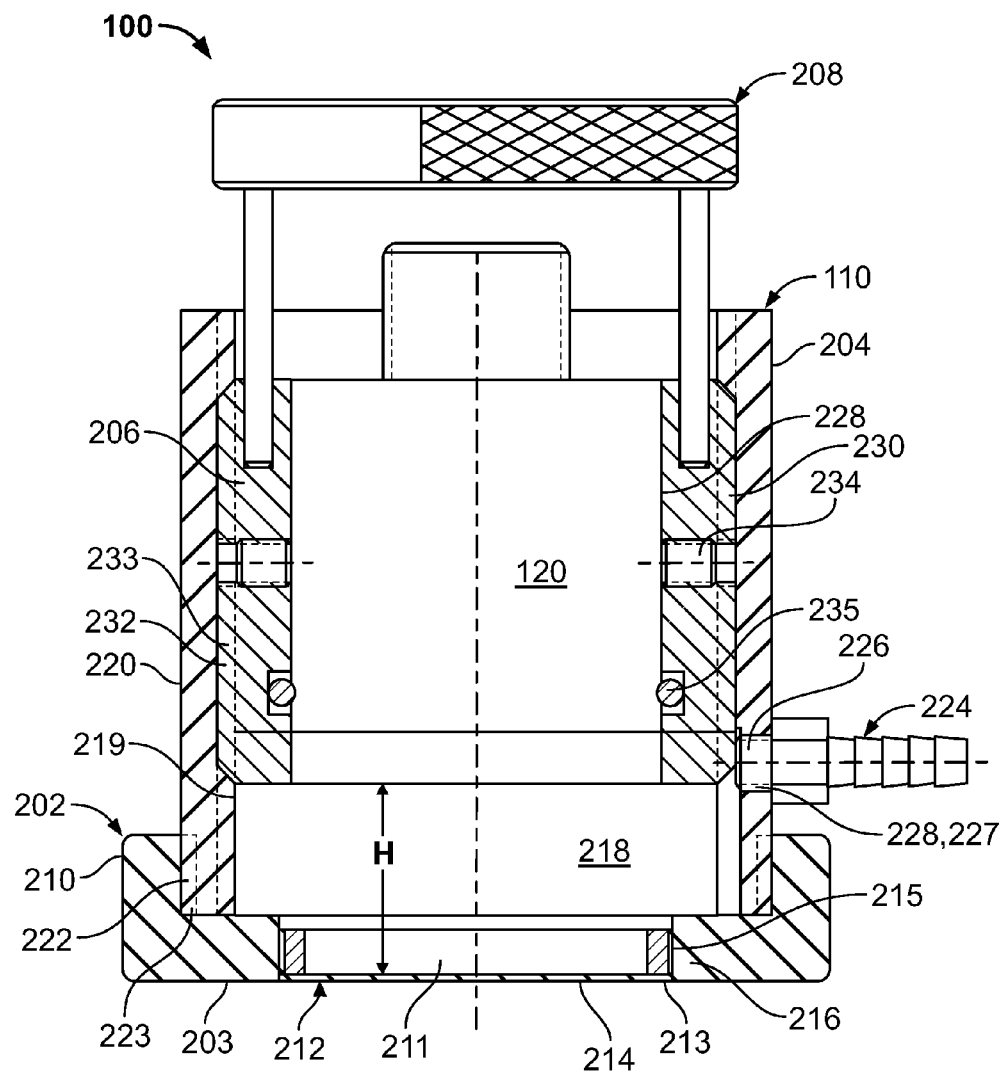
FIG. 2 is a cross sectional view of the ultrasonic testing device of FIG. 1.

FIG. 2 shows a cross-sectional view of the UT device 100 of FIG. 1. As can be seen in FIG. 2, the housing 110 includes a scanning shoe 202, an outer housing 204, an inner housing 206, and a height adjustment control device 208. The scanning shoe 202 includes a base 210 and a flow control device 212. The base 210 includes a bottom surface 203 having an opening 211. The base 210 provides alignment of the housing 100 in relationship to the test article 160 (FIG. 1), assists the UT device 100 in traversing the test article 160, and increases the distance that the ultrasonic signal must travel from the transducer 120 to the inspection surface 150 (FIG. 1).

The flow control device 212 includes a housing 213 and a permeable membrane (membrane) 214 having perforations 214a. The housing 213 includes threads or other compressible interfaces 215 that are releasably received by the base 210. The membrane 214 is attached to the base 210 by overlapping the membrane 214 over threads or a compressible interference fit 215 and then inserting the housing 213 into the base 210 by engaging threads 215 with grooves 216 on the inside surface 217 of the base 210 to secure the membrane 214 to the scanning shoe 202. In another embodiment, the membrane 214 may be attached directly to the housing 212. In another embodiment, the membrane 214 may be directly attached to the base 210. In another embodiment, the flow control device 212 may be attached to the scanning shoe 202 by clips, fasteners or other attachment devices.

The membrane 214 is formed of a permeable, perforated, polymer film having a plurality of perforations (not shown). In an embodiment, the membrane 214 may be formed of perforated latex, nitrile, vinyl, cellophane (tape) or PTFE. The membrane 214 is preferably thin and of low acoustic impedance comparable to that of water so that the ultrasonic waves pass through the membrane 214 with little attenuation. The membrane 214 partially defines a non-contact fluid chamber 218.

The permeability and/or number of perforations are selected to control the flow rate of fluid released from the non-contact fluid chamber 218, and thus, the amount of fluid forming contact with the inspection surface. Other membrane designs are possible. In another embodiment, the membrane 214 is permeable not because it contains perforations, but because the material itself is porous, such as gels or screens with very small openings.

In another embodiment, the scanning shoe 202 may include roller guides (not shown) that can be used to facilitate movement, for example, along the scan direction. The roller guides may be wheels, skids or other similar motion assist devices. In an embodiment, the roller guides may retard any undesired lateral motion (e.g. in the index direction).

The outer housing 204 is attached to the scanning shoe 202. The outer housing 204 has a generally cylindrical geometry and includes an inside surface 219 and outside surface 220. The inside surface 219 partially defines fluid chamber 218. The fluid chamber 218 has an adjustable height H. The outside surface 220 includes threads 222.

The outer housing 204 is attached to the base 216 of the scanning shoe 202 by threads 222 that engage grooves 223 of base 216. The threads 222 form a fluid seal with the scanning shoe 202. In another embodiment, seals, o-rings, tape, sealant or other sealing devices or methods may be used to seal the outer housing 204 to the scanning shoe 202 to prevent or to reduce the loss of fluid from the fluid chamber 218. In another embodiment, the outer housing 204 and base 216 may be a single component.

A fluid coupling 224 is releasably attached to an opening 226 in the outer housing 204 by threads 227. In another embodiment, the fluid coupling 224 may be attached to the outer housing 204 by another fastening system, such as a quick release couple or the like. In another embodiment, the fluid coupling 224 may be an integral part of the outer housing 204. The fluid coupling 224 releasably receives the fluid line 140 (FIG. 1). The fluid coupling 224 receives fluid from the fluid line 140.

The inner housing 206 is adjustably connected or coupled to the outer housing 204. The inner housing 206 has a generally cylindrical geometry. The inner housing 206 includes an inside surface 228 and an outside surface 230. The inside surface 228 at least partially defines the transducer cavity 214. The outside surface 230 includes threads 232 that engage grooves 233 on the inside surface 219 of the outer housing 204. The variable height H of the fluid chamber 218 may be adjusted by rotating the inner housing 206 to withdraw or insert the inner housing 206 from or into the outer housing 204. In such a manner, the housing 110 can be expanded or contracted to vary the variable height H. The variable height H can be adjusted to change the height of the water column in the fluid chamber 218 so as to vary the focal length of the transducer 120 and the length of the UT signal path. In FIG. 1, the inner housing 206 is shown in a fully inserted position that results in a minimum adjustable height H.

In another embodiment, the thread 232 and groove 233 arrangement may be reversed, or in other words, the threads may be on the outer housing 204 and the grooves may be on the inner housing 206. In another embodiment, the outer housing 204 may be adjustably connected to the inner housing 206 by guides, rails, and/or another sliding or adjustable coupling mechanism that allows for the inner housing 206 to be incrementally withdrawn/inserted from the outer housing 204.

The inner housing 206 includes fasteners 234 that releasably secure the transducer 120 within the inner housing 206. In this exemplary embodiment, the fasteners are set screws. In another embodiment, the fasteners 234 may be screws, clips, retainers or other similar retaining devices. The inner housing also includes a fluid seal 236 that prevents fluid from flowing past the transducer 120 and inner housing 206.

The adjustment control device 208 is attached to the inner housing 206 and may be used by an operator (not shown) to rotate the inner housing 206. The adjustment control device 208 includes an opening 238 that allows for the passing of the signal transmission link 130 (FIG. 1) through opening 238 and to the transducer 120. In another embodiment, the adjustment control 208 may have another shape, such as, but not limited to a knob, rod or other graspable protrusion extending from the inner housing 206. In another embodiment, the adjustment control device 208 may be omitted and an operator may directly rotate the inner housing 206 to adjust its degree of insertion and withdrawal.

The transducer 120 may be an ultrasonic array, phased ultrasonic array, linear array probe, single transducer probe, or other type of probe that is electronically scanned along one dimension. In an embodiment, the same probe (i.e., same transducer element(s)) acts as both the transmitter and the receiver. In another embodiment, different probes (i.e., different transducer elements) can be used as transmitter and receiver.

Figure 2A:
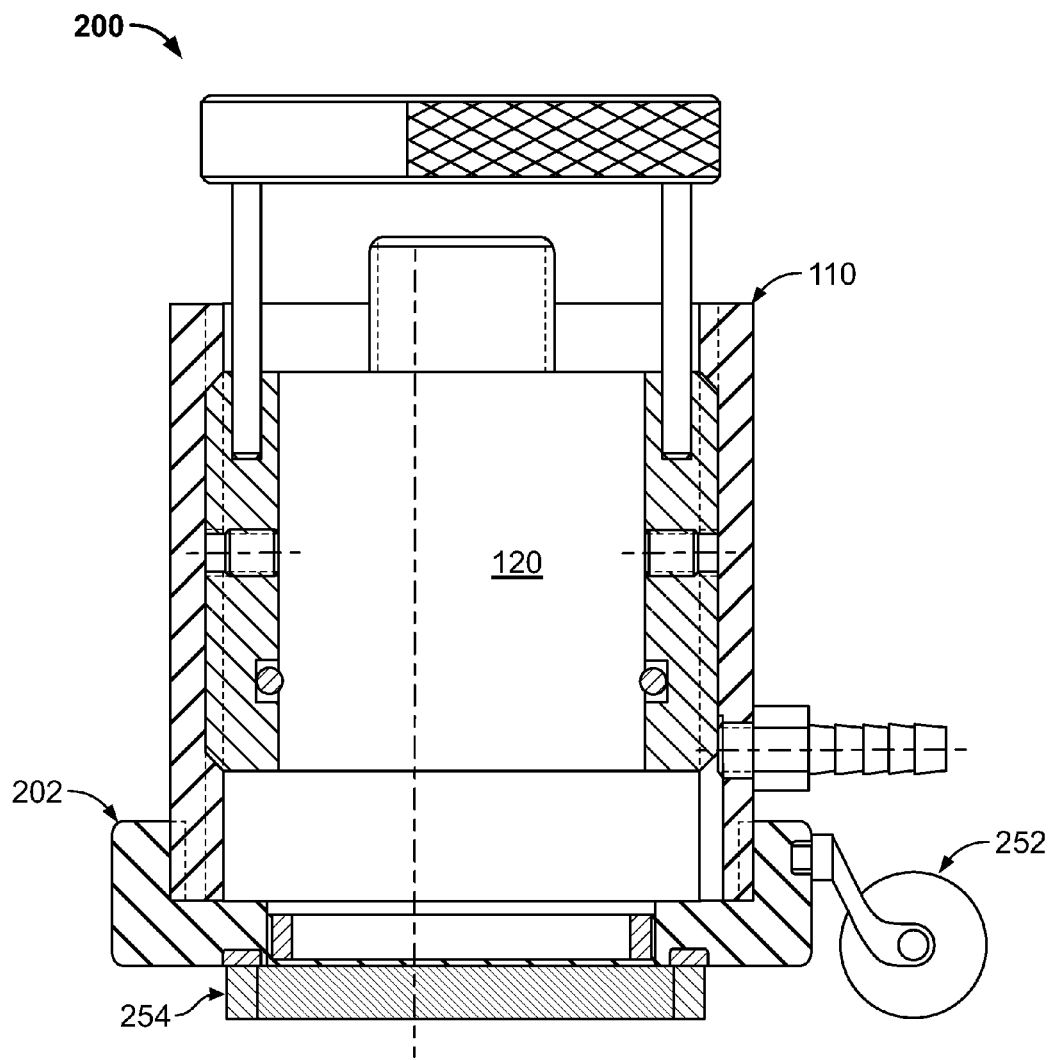
FIG. 2A shows another embodiment of an ultrasonic testing device according to the present invention.

FIG. 2A shows another embodiment of the UT device 100. In this embodiment, the UT device 100 includes an optional wheel encoder 252 attached to the scanning shoe 202. The wheel encoder 252 is used to determine and record the position of the UT probe in a single axis (single direction). This position information is then linked with the associated inspection results at each point to allow for the production of a C-scan image. Alternatively, an optical encoder may be placed at this location to record the probe position in both X and Y directions. This would allow for the production of a C-scan that covers any random portion of the inspection surface as controlled by the inspector moving the probe along any path.

Figure 5:
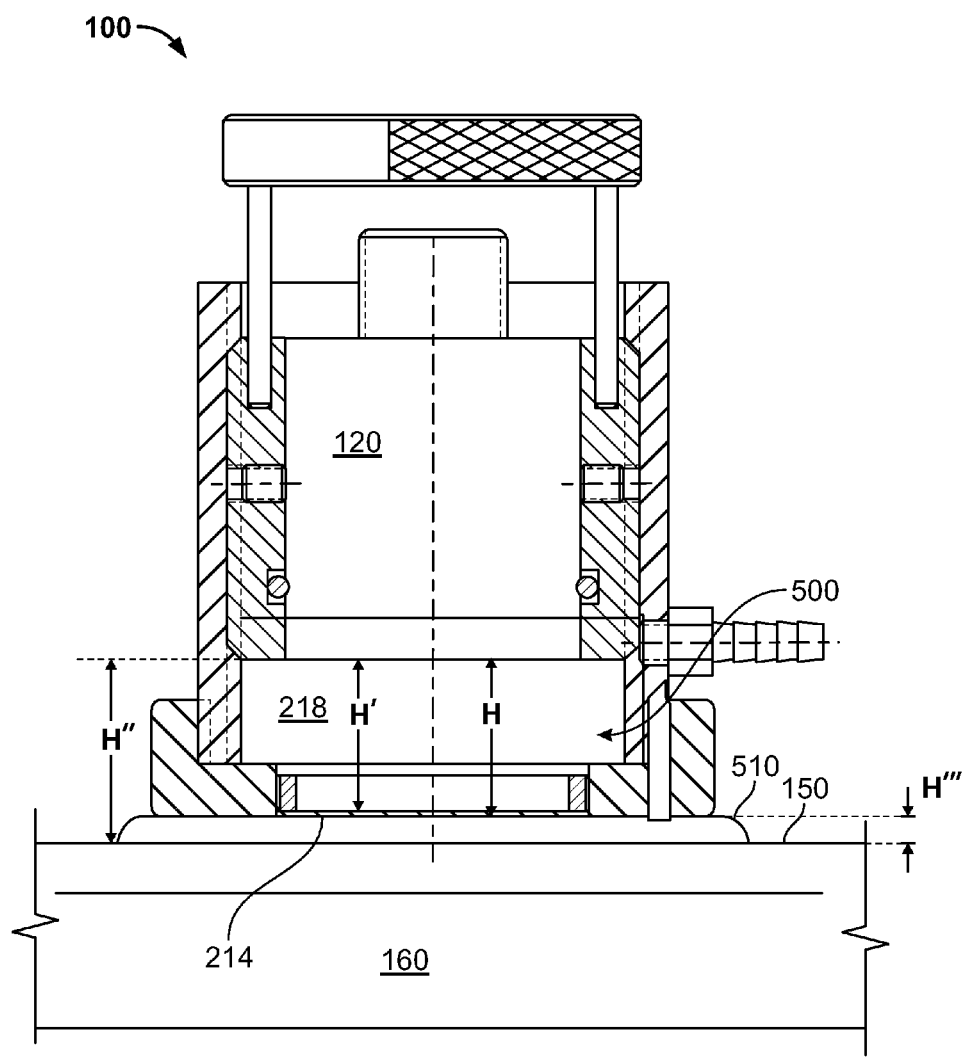
FIG. 5 is a cross sectional view of the ultrasonic testing device of FIG. 1 while scanning a test article.

In this embodiment, the scanning shoe 202 also includes an optional seal 254 that controls the spread of the fluid pool 510 (FIG. 5). In this exemplary embodiment, the seal 254 is a gasket. In another embodiment, the seal 254 may be a brush, gasket or other malleable structure that controls the flow of fluid in the couplant pool. The seal 254 is attached to the bottom side of the base 210 and forms a liquid seal around the inspection site by constricting the flow of the liquid onto the inspection surface. The seal 254 conforms to unevenness in the inspection surface, although it may not be perfectly conforming and may not be perfectly sealing.

Figure 3:
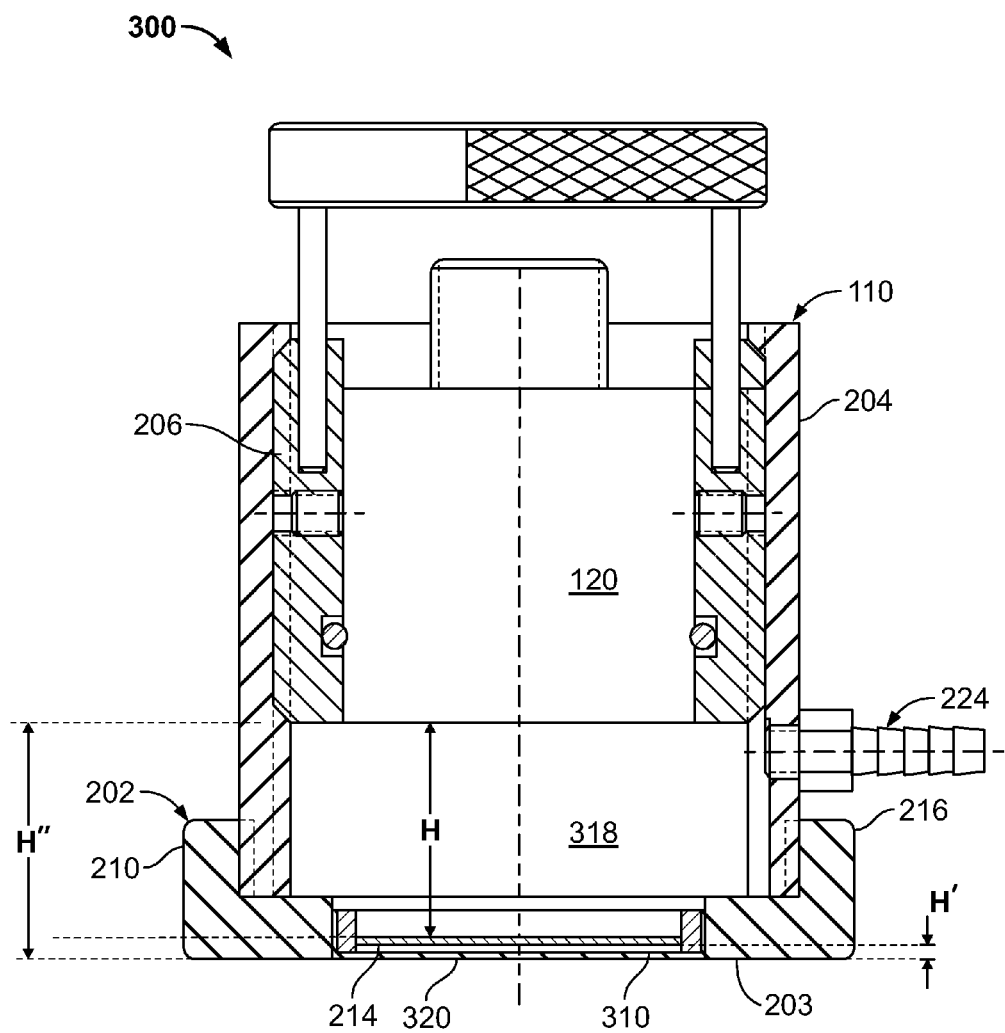
FIG. 3 is a cross sectional view of another embodiment of an ultrasonic testing device according to the invention.

FIG. 3 shows another embodiment of an UT device 300 according to the invention. As can be seen in FIG. 3, the inner housing 206 has been partially raised or withdrawn to increase the adjustable height H of the fluid chamber 212 when compared to the adjustable height H of FIG. 2. Also in this embodiment, the membrane 214 is not located flush or adjacent to the bottom surface 203 of the scanning shoe 210 as shown in FIG. 2, but instead is located within the scanning shoe 210. In such a manner, the membrane 213 divides the fluid chamber 216 into a non-contact fluid chamber 318 and a contact fluid chamber 320. The contact fluid chamber 320 has a contact fluid height H'. The UT device 300 has a total fluid height H" that includes the variable height H and the contact fluid height H'.

The fluid coupling 224 provides liquid to the non-contact fluid chamber 318, and the membrane 214 permits flow of the liquid from the non-contact fluid chamber 318 to the contact fluid chamber 320. The non-contact fluid chamber 318 preferably has a greater volume than the contact chamber 320, and the ultrasonic wave path preferably is longer in the non-contact chamber 310 than in the contact chamber 320. In this way, the majority of liquid resides in the non-contact fluid chamber 318, which is better contained than the fluid in the contact fluid chamber 320. The permeability of the membrane 214 may be selected to determine flow between the two chambers.

Figure 4:
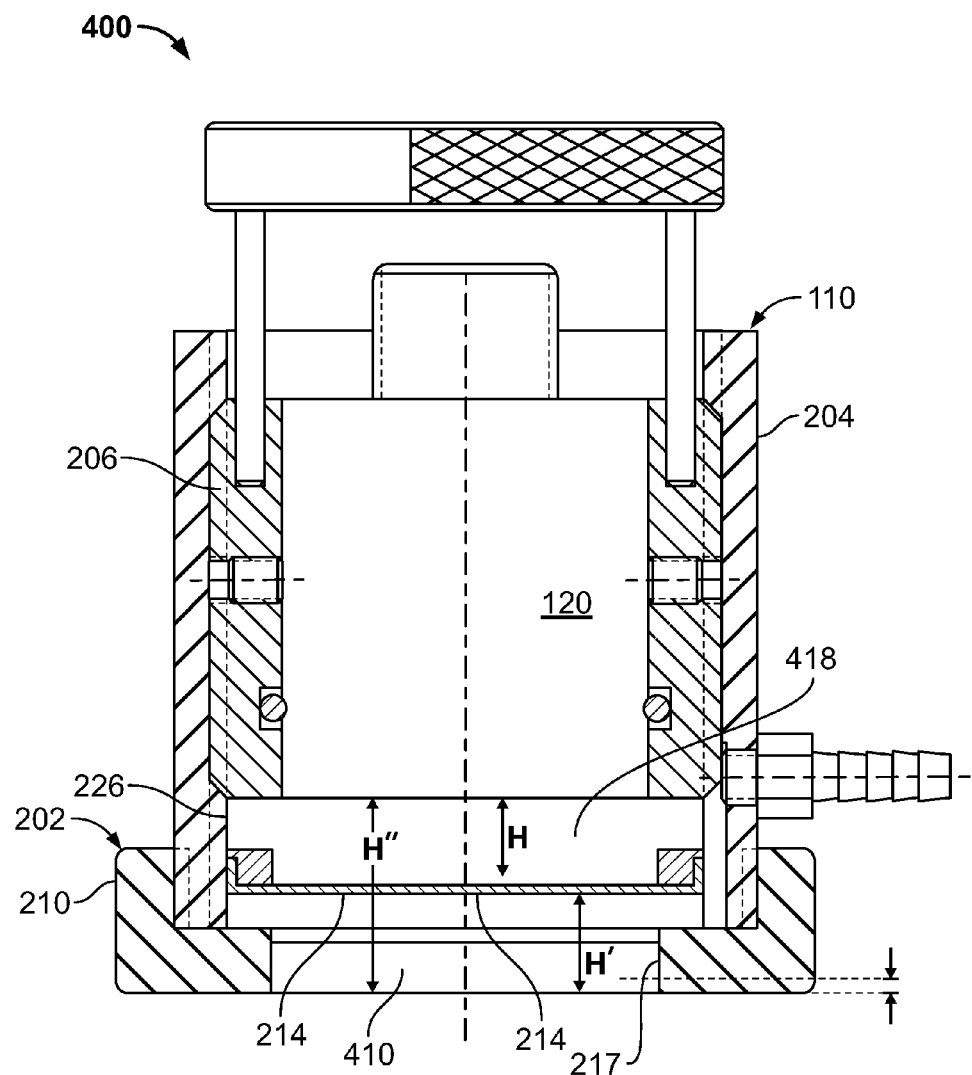
FIG. 4 is a cross sectional view of another embodiment of an ultrasonic testing device according to the invention.

FIG. 4 shows another embodiment of an UT device 400 according to the invention. As can be seen in FIG. 4, the membrane 214 has been raised within the outer housing 204, resulting in the contact fluid chamber 420 being at least partially defined by the inside surface 226 of the outer housing 204 and the inside surface 217 of the base 210. The contact fluid chamber 410 has a contact fluid height H'.

FIG. 5 shows the UT device 100 during a scanning operation. As can be seen in FIG. 5, a fluid 500 has been introduced into non-contact fluid chamber 218 from fluid line 140 (FIG. 1). In this exemplary embodiment, the fluid 300 is water. In another embodiment, the fluid 300 may be any type of liquid medium that produces an ultrasonic impedance match with the component being inspected, and may include additives such as, but not limited to dissolved oils and gels. A fluid pool 510 is formed between the UT device 100 and the test surface 150. The fluid pool 310 is formed from fluid 300 that has passed through the membrane 214 from the fluid chamber 218. The fluid pool 310 forms a transmitive couple between the UT device 100 and the test article 160. In such a manner, ultrasonic waves are propogated to and from the transducer 120 to the test article 160. The fluid pool 310 has a fluid pool height H''' that adds to the adjustable height H to form the total fluid height H".

Figure 6:
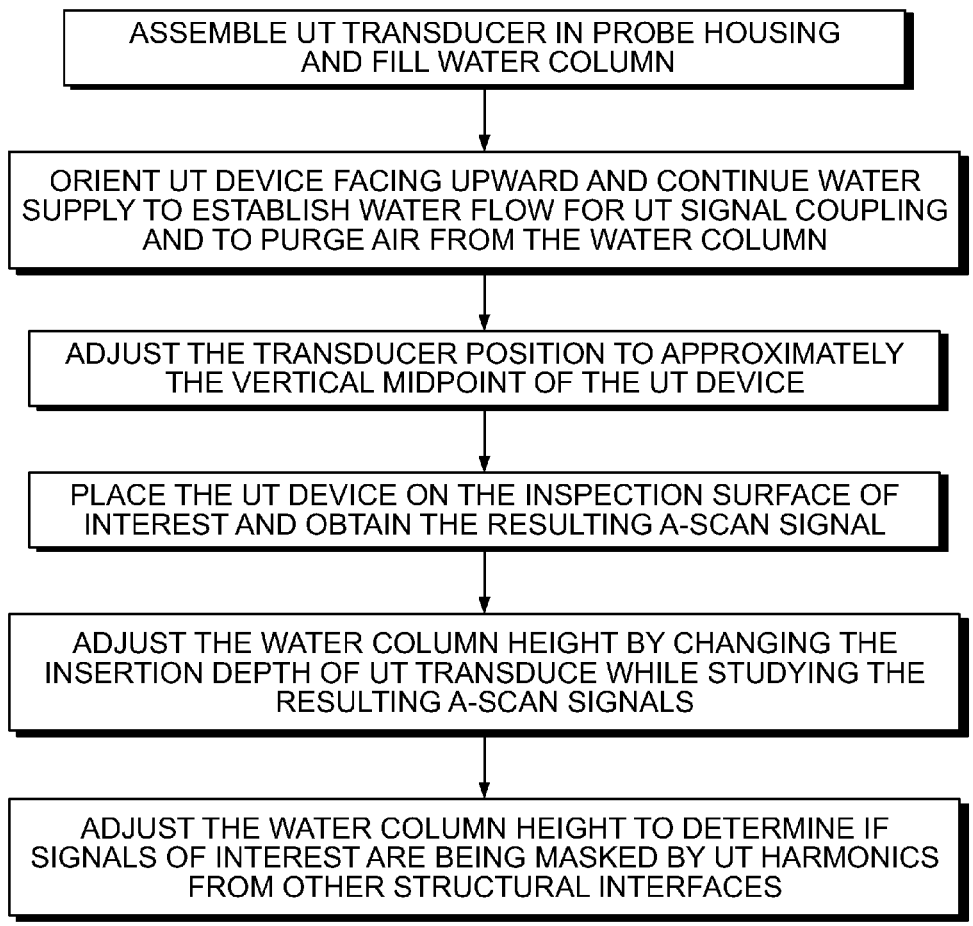
FIG. 6 is a flowchart showing setup and use of a UT device according to the present invention.

FIG. 6 shows the steps of an embodiment of a method of inspecting an article according to the present invention. In this embodiment, a UT device as shown in FIG. 1 having the membrane flush with the bottom surface of the scanning shoe was used. As can be seen in FIG. 6, a first step 610 includes assembling the UT device by placing an ultrasonic transducer in the device housing and filling the non-contact fluid chamber with a fluid.

According to a second step 620, the UT device is oriented so that the bottom of the scanning shoe is facing upward (the membrane is facing upward) while continuing to supply fluid to the non-contact fluid chamber until fluid is flowing from the membrane, thus purging the non-contact fluid chamber of air.

According to a third step 630, the transducer position within the housing is adjusted by adjusting the insertion depth of the inner housing within the device to approximately the mid-point of the adjustable fluid column height. This step may be performed before or after the first step 610.

According to a fourth step 640, the UT device is placed upon an inspection surface of interest and an initial A-Scan signal is produced.

Figure 7A:
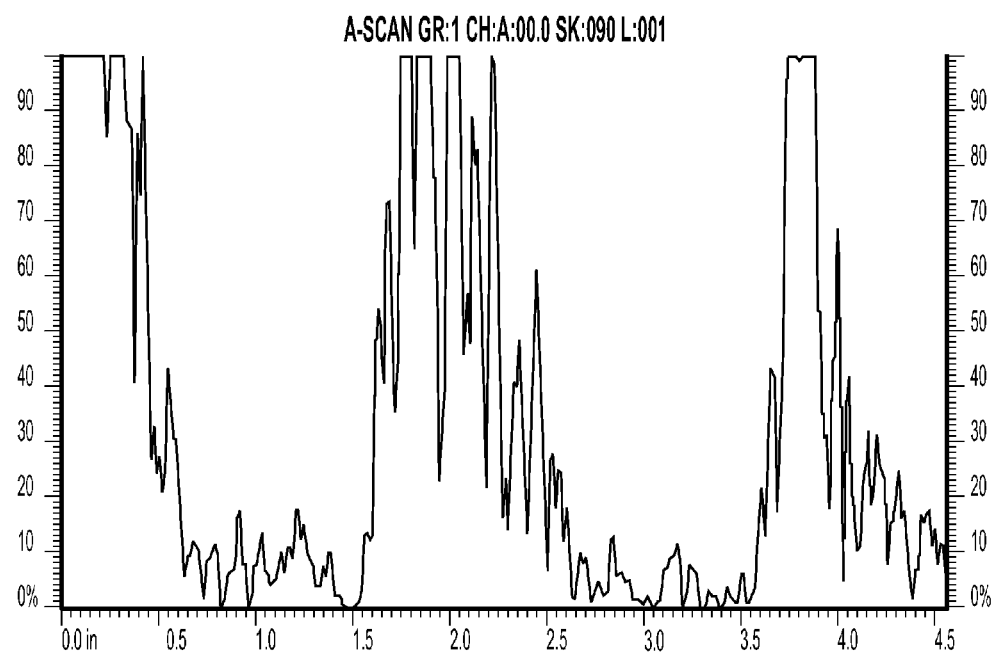
FIG. 7A is an A-scan showing the harmonic signal from the front surface completely hiding the backwall signal of interest.
Figure 7B:
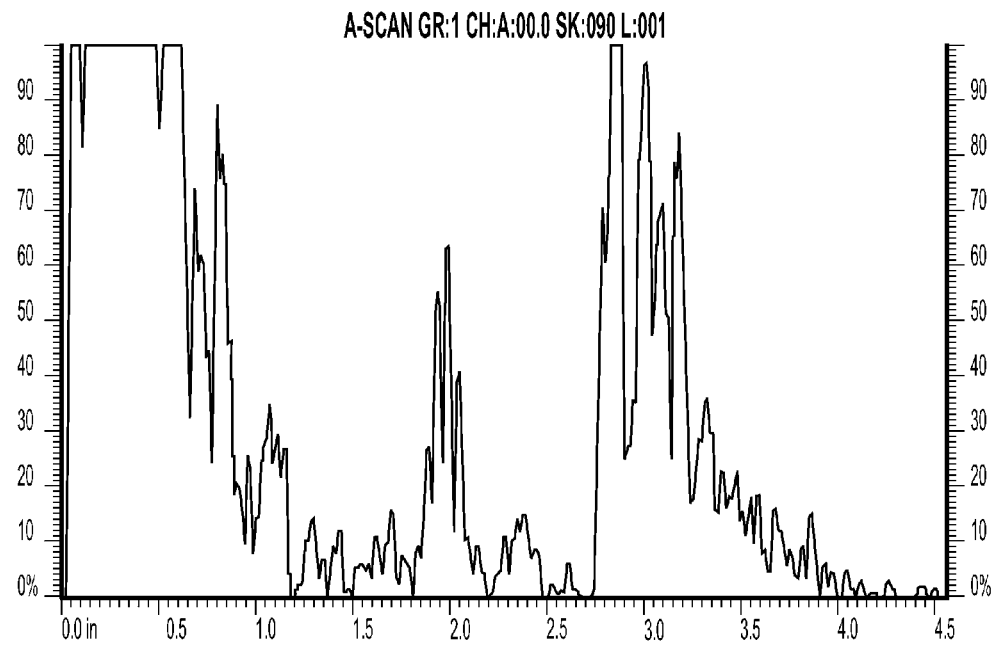
FIG. 7B is an A-scan having the water column height adjusted to move the harmonic signal from the front surface out in time to reveal the backwall signal of interest.

FIG. 7A shows the results of an initial A-Scan signal with the water column height set at 25 mm. As can be seen in FIG. 7A, the front surface harmonic signal completely hides or masks the backwall signal of interest.

Referring again to FIG. 6, according to a fifth step 650, the water column height was adjusted, both increased and decreased, while observing the resulting A-Scan signals.

According to a sixth step 660, the water column height was determined to be at an optimal height at 40 mm to observe the harmonic signal from the backwall of the inspection object. In such a manner, the transducer delay or offset was adjusted so as to unmask the backwall signal of interest, thereby producing an optimum water column height and transducer position for this A-Scan.

In an embodiment, the method includes moving an UT device across a surface of the article while interrogating the article with ultrasonic waves. In another embodiment, the UT device is held stationary, and the article to be inspected is moved past the UT device. For example, the UT device may be held in a relatively stationary position while parts on an assembly line travel past the probe.

The height of the ultrasonic-transmitting liquid may be adjusted in real-time while scanning the article. The height of the ultrasonic-transmitting liquid may be adjusted by adjusting the liquid height contained in the fluid cavity of the housing of the UT device. In such a manner, the height of the liquid may be adjusted to focus the ultrasonic waves. Also, in adjusting the water column height the signals of interest (typically the backwall signal of the part) can be separated from the front wall signal multiples created by the impedance mismatch between the liquid column and the part being inspected. Increasing the column height pushes the front wall multiple signals further out in time, enhancing signal clarity and associated scans. Typically, as the part increases in thickness the water path height or stand-off needs to be increased. Inversely, as the part thins the water column height may be decreased.

Ultrasonic waves follow an ultrasonic wave path from the transducer, through the fluid column, and to an inspection site on the inspection surface and then back to the transducer. If an area scan is desired, the device can be designed to move in the perpendicular direction (which shall be referred to as the scan direction). In an embodiment, an encoder (not shown) records and relates the position of the device as it is moved along the scan direction. This allows for the production of C-Scan type of color-coded maps that show the presence and allow the measurement of flaws and defects, or otherwise show changes in the material.

The ultrasonic transducer uses a single transducer that functions as both the transmitter and the receiver, a two-dimensional (X-Y)C-Scan can be produced by running the transducer in the X-direction while also incrementing the location of the scan lines in the Y-direction. Phased array ultrasonic probes contain a linear array of independent ultrasonic transducers in the Y-direction so that a single X-direction scan can produce an area mapping (paint brush approach) contributing to reducing the time required for inspecting an area. Phased array ultrasonic probes also provide for increased resolution and sensitivity compared to conventional spot probe transducers.

In another embodiment, area ultrasonic arrays may be used to increase the scanning speed or to provide redundant measurements. In another embodiment, the UT device may be a spot probe that is mechanically moved in two dimensions, optionally with a corresponding two-dimensional position encoder. Various position encoders such as rotary wheel encoders, string encoders, or linear variable differential transformers (LVDT) can be used. Encoder devices incorporated into the probe holder assembly can allow for complete area mapping of an inspection surface. This facilitates the production of C-scan color-coded maps that show the presence of flaws or other changes in the material.

In another embodiment, conventional pulse-echo ultrasonics, pulses of high frequency sound waves are introduced into a structure being inspected. A-Scan signals represent the response of the stress waves, in amplitude and time, as they travel through the material. As the waves interact with defects or flaw interfaces within the solid and portions of the pulse's energy are reflected back to the transducer, the flaws are detected, amplified and displayed. The interaction of the ultrasonic waves with defects and the resulting time vs. amplitude signal depends on the wave mode, its frequency and the material properties of the structure. Flaw size can be estimated by comparing the amplitude of a discontinuity signal with that of a signal from a discontinuity of known size and shape. Flaw location (depth) can be determined from the position of the flaw echo along a calibrated time base.

In pitch-catch ultrasonics, one probe introduces a pressure wave into the specimen and a second probe detects the transmitted wave. A complex wave front is generated internally in the material as a result of velocity characteristics, acoustical impedance, and thickness. The time and amount of energy is affected by the changes in material properties, such as thickness, disbonds, and discontinuities. The mechanical vibration (ultrasound) is introduced into the specimen through a couplant and travels by wave motion through the specimen at the velocity of sound. If the pulses encounter a reflecting surface, some or all of the energy is reflected and monitored by the probe. The reflected beam, or echo, can be created by any normal or abnormal (flaw) interface. Complete reflection, partial reflection, scattering, or other detectable effects on the ultrasonic waves can be used as the basis of flaw detection.

Flaw and damage detection can also be achieved by taking the A-Scan signals and transforming them into a single C-Scan image of the part being inspected. C-Scan technology uses information from single point A-Scan waveforms to produce an area mapping of the inspection surface. These two-dimensional images can be produced by digitizing point-by-point signal variations of an interrogating sensor while it is scanned over a surface. C-Scan area views provide the inspector with easier-to-use and more reliable data with which to recognize flaw patterns. This format provides a quantitative display of signal amplitudes or time-of-flight data obtained over an area. The X-Y position of flaws can be mapped and time-of-flight data can be converted and displayed by image processing equipment to provide an indication of flaw depth. A variety of PC-based manual and automated scanning devices can provide position information with digitized ultrasonic signals. Specific emphasis can be placed on portions of the ultrasonic signal and highlighted in a color-mapped C-Scan, based on user specified amplitude gates, time-of-flight values and signal waveforms.

Various modalities can also be used. Examples of pulse-echo, pitch-catch, longitudinal waves and shear waves were described above. In addition, another type of ultrasonic wave is the Lamb wave. The Lamb wave can be introduced in a number of ways. Wave mode conversion can occur at changes within the structure.

Finally, although the disclosure above was described in the context of inspecting adhesive bonds on composite blades, the invention is not limited to this application. Structural joints, both composite and metallic, can also be inspected. In general, the approaches described above can be applied to any material and structural configuration that lends itself to ultrasonic inspections (e.g. composite materials, metallic structures, ceramics, concrete). Other examples include the inspection of various joining methods: resistance spot welds, friction stir welds, self-piercing rivets and clinch joining to name a few. Ultrasonic inspection can also be used for surface indentation/cosmetic quality of surfaces, leak testing by looking for breaks in a seal, and acoustic testing in the form of looking for coupling between surfaces.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

What is claimed is:

1. An ultrasonic testing device, comprising:
   a housing system comprising:
      an outer housing;
      an inner housing adjustably connected to the outer housing;
   a transducer disposed within the inner housing;
   wherein the outer housing comprises an interior surface that at least partially defines a fluid cavity having a water column height; and
   wherein the inner housing is incrementally adjustably connected to the outer housing to increase and decrease the water column height.

2. The ultrasonic testing device of claim 1, wherein the inner housing is adjustably connected to the outer housing by threads that allow the inner housing to be inserted into and withdrawn from the outer housing.

3. The ultrasonic testing device of claim 1, further comprising:
   a permeable membrane that further at least partially defines the fluid cavity.

4. The ultrasonic testing device of claim 1, further comprising:
   an external fluid supply connected to the outer housing that provides a continuous flow of a UT coupling fluid between the transducer and a surface of a component being inspected.

5. The ultrasonic testing device of claim 1, further comprising at least one fluid seal between the outer housing and the inner housing.

6. A method of ultrasonic inspection, comprising:
   placing an ultrasonic inspection device having an adjustable fluid column height upon a test article; wherein the ultrasonic inspection device comprise an inner housing adjustably connected to an outer housing and a transducer disposed within the inner housing;
   providing fluid to the ultrasonic inspection device;
   generating ultrasonic waves from the transducer within the ultrasonic inspection device; and
   incrementally adjusting the fluid column height by withdrawing or inserting the inner housing into the outer housing to perform an ultrasonic inspection scan of an article.

7. The method of claim 6, wherein the ultrasonic inspection device includes a housing, and the fluid column height is adjusted by expanding or contracting the housing.

8. The method of claim 7, wherein the housing comprises an inner housing and an outer housing, the housing is expanded or contracted by partially withdrawing or inserting the inner housing from or into the outer housing, respectively.

9. The method of claim 6, wherein the fluid column height is adjusted during the ultrasonic inspection scan.

10. The method of claim 6, wherein the fluid column height is the distance from the transducer to a permeable membrane.

* * * * *